United States Patent [19]

Jessop et al.

[11] Patent Number: 4,794,085

[45] Date of Patent: Dec. 27, 1988

[54] APPARATUS AND METHOD FOR DETECTING LIQUID PENETRATION BY A CONTAINER USED FOR ASPIRATING AND DISPENSING THE LIQUID

[75] Inventors: Thomas C. Jessop, Webster; Raymond L. Nelson; Rodney J. Whitcomb, both of Rochester, all of N.Y.

[73] Assignee: Eastman Kodak Company, Rochester, N.Y.

[21] Appl. No.: 80,146

[22] Filed: Jul. 29, 1987

Related U.S. Application Data

[63] Continuation of Ser. No. 632,516, Jul. 19, 1984, abandoned.

[51] Int. Cl.⁴ .............................................. G01N 35/00
[52] U.S. Cl. .................................... 436/54; 73/863.01; 422/63; 422/64; 422/65; 422/67; 422/100; 436/49; 436/180
[58] Field of Search ................... 73/863.01, 864.24; 137/386; 141/94, 95, 250; 318/685, 592–594; 364/182; 422/63–67, 73, 100; 436/49, 54, 180

[56] References Cited

U.S. PATENT DOCUMENTS

| | | | |
|---|---|---|---|
| 3,754,444 | 8/1973 | Ure et al. | 73/863.01 |
| 3,894,438 | 7/1975 | Ginsberg | 73/863.01 |
| 3,992,158 | 11/1976 | Przybylowicz et al. | 422/57 |
| 4,041,995 | 8/1977 | Columbus | 141/275 |
| 4,053,381 | 10/1977 | Hamblen et al. | 204/195 M |
| 4,258,001 | 3/1981 | Pierce et al. | 422/56 |
| 4,287,155 | 9/1981 | Tersteeg et al. | 422/64 |
| 4,340,390 | 7/1982 | Collins et al. | 422/64 |

FOREIGN PATENT DOCUMENTS

| | | | |
|---|---|---|---|
| 56-164957 | 12/1981 | Japan | 422/100 |
| 56-164958 | 12/1981 | Japan | 422/100 |
| 59-52759 | 3/1984 | Japan. | |

*Primary Examiner*—Michael S. Marcus
*Attorney, Agent, or Firm*—Dana M. Schmidt

[57] ABSTRACT

Apparatus and a method are described which permit the detection of penetration of liquid by an apertured container used for aspirating and dispensing the liquid. The apparatus and method feature control means for advancing the container an increment of the maximum possible distance to the liquid; generating a pressure differential within the dispensing container that is sufficient to generate a signal that is indicative of whether the container aperture is closed by the liquid; detecting and signalling the pressure produced within the container by such a pressure differential; and comparing such signalled pressure against a reference value determinative of whether the container has penetrated the liquid.

18 Claims, 4 Drawing Sheets

APPARATUS AND METHOD FOR DETECTING LIQUID PENETRATION BY A CONTAINER USED FOR ASPIRATING AND DISPENSING THE LIQUID

This is a continuation of application Ser. No. 632,516, filed July 19, 1984, now abandoned.

FIELD OF THE INVENTION

This invention relates to the aspiration of liquid into a container from which it is dispensed. More specifically, it relates to the detection of when it is appropriate to commence such aspiration.

BACKGROUND OF THE INVENTION

Liquid dispensers have been used in analyzers for the detection of the concentration of liquid analytes using as analysis means, test elements that contain within themselves the necessary reagents to permit such detection. Examples of such analyzers are described in U.S. Pat. Nos. 4,287,155, issued Sept. 1, 1981, and 4,340,390, issued July 20, 1982. Examples of such test elements appear in U.S. Pat. Nos. 3,992,158, issued Nov. 16, 1976., 4,053,381, issued Oct. 11, 1977; and 4,258,001, issued Mar. 24, 1981. The conventional method for dispensing liquid onto such test elements using such analyzers has been to aspirate test liquid from a relatively large container, into a dispensing container. The dispensing container is then moved to a position immediately above such a test element, and a fraction (e.g., 10 $\mu$l) of the aspirated liquid is dispensed. The dispensing container is fluidly connected, in such analyzers, to a pressurizing means that generates both the operative partial vacuum needed to aspirate the needed amount of liquid into the container, and the partial pressure operative to dispense that aspirated liquid, in fractional amounts, onto a plurality of test elements. A pressure transducer is also conventionally included to ascertain the pressure within the container, so as to detect the occurrence of the desired dispensing event versus a failure to dispense. A microprocessor generally is used to control the apparatus in response to the conditions sensed.

Such conventional analyzers include a motor for raising and lowering the dispensing container, removably mounted on a probe, relative to the large container that supplies the test liquid. Such motors usually are preset to move the dispensing container a fixed distance into such large containers. This has functioned well when the level of the liquid within such large containers has been generally constant, and therefore predictable. However, usually the level is not constant. That is, although the large containers usually have a prescribed protocol that governs their filling, in the case where the dispensing apparatus is used for clinical analysis of body fluids, operators find it more convenient to overfill. Even the overfill is not necessarily constant. Because of the lack of predictability, the motor is preset to accommodate the lowest possible liquid level as the "nominal" liquid level. Unfortunately, this means that the exterior of the dispensing container becomes excessively wetted with the test liquid in those containers having more, and especially those with much more, than the minimum volume providing such lowest level. It has been found that such excessive wetting tends to encourage perfusion during subsequent dispensing. As used herein, "perfusion" means movement of the liquid being dispensed, up the exterior surface of the dispensing container, rather than down onto the test element. As is readily apparent, such perfusion prevents some or all of the desired test liquid from reaching the test element.

What then has been needed is a way of detecting when the dispensing container has penetrated the air-liquid interface within the large container. Although electrical contact of an electrically conductive dispensing container and the test liquid has been used in prior devices, such a technique requires dispensing containers made of especially conductive materials, which therefore become a permanent part of the device. In contrast, the dispensing containers disclosed in the aforesaid analyzer patents have been disposable after each test sample has been dispensed onto one or more test elements. Disposability is practically essential to prevent one test sample from contaminating another.

U.S. Pat. No. 3,894,438 discloses yet another method of detecting the penetration of the air liquid interface. In that patent, the sampling probe is provided with a sensing probe that is separate from but connected to the sampling probe so that the sensing probe enters the liquid phase after the sampling probe. A separate gas source is provided to the sensing probe, to cause an air stream to issue from the sensing probe. When the sensing probe reaches the air-liquid interface, the resistance to the outflowing air changes, and this change in pressure generates a signal that is indicative of the penetration having occurred.

The approach described in the '438 patent does permit the use of disposable dispensing containers. However, one drawback of such an approach is that it requires a second probe besides the sampling probe. Furthermore, a separate gas supply is also needed.

Thus, prior to this invention there has been a need for a simple mechanism for detecting the location of the air-liquid interface in sample supply containers having varying levels of liquids, that permits the use of disposable dispensing containers.

SUMMARY OF THE INVENTION

This invention is based upon the discovery that the penetration of the air-liquid interface can be sensed using, in part, the dispensing apparatus used to dispense the liquid.

More specifically, there is provided an aspirating control system in apparatus for aspirating and dispensing liquid and including a probe for removably mounting a container having an aspirating and dispensing aperture; pressurizing means fluidly connected to the probe for generating an operative pressure differential, relative to atmospheric pressure, within a mounted container; and moving means for advancing the probe and such mounted container toward, and away from, a nominal liquid level location. The control system comprises (a) means for controlling the advance of the probe in increments, (b) means for actuating the pressurizing means to generate a pressure differential in such container, relative to atmospheric pressure, that is sufficient to indicate whether such container aperture is closed by the liquid, (c) means for detecting and signalling the pressure produced within such container by the pressure differential; and (d) means for comparing the signalled pressure against a reference value determinative of the presence of liquid in the container aperture.

In accord with another aspect of the invention, there is provided a method for detecting penetration of an air-liquid interface by an aspirating and dispensing apparatus, comprising the steps noted for the means (a) through (d) recited in the previous paragraph.

Thus it is an advantageous feature of the invention that no additional air supply or sensing probe is required besides the pressurizing means and probe already used to aspirate and then dispense the aspirated liquid, to detect in a controlled manner for disposable dispensing containers, whether penetration of the liquid by the dispensing container has occurred.

It is a related advantageous feature of the invention that a minimum amount of external wetting of the dispensing container is required for aspiration, thereby reducing perfusion.

Other advantageous features will be readily apparent from the following Description of the Preferred Embodiments when read in light of the attached drawings.

DESCRIPTION OF THE PREFERRED EMBODIMENTS

The invention is particularly useful in colorimetric and potentiometric assays using analyzers and dried test elements of the type described in the above-noted patents. In addition, the invention is useful in any dispensing apparatus or method which aspirates liquid after moving the dispensing container from the atmosphere into a liquid phase, regardless of the steps that follow the dispensing of the aspirated liquid.

Terms such as "up", "down", "lower", "vertical", "horizontal", and "bottom", as used herein refer to the orientation of parts when the apparatus is positioned in its customary position of use.

Figure 1:
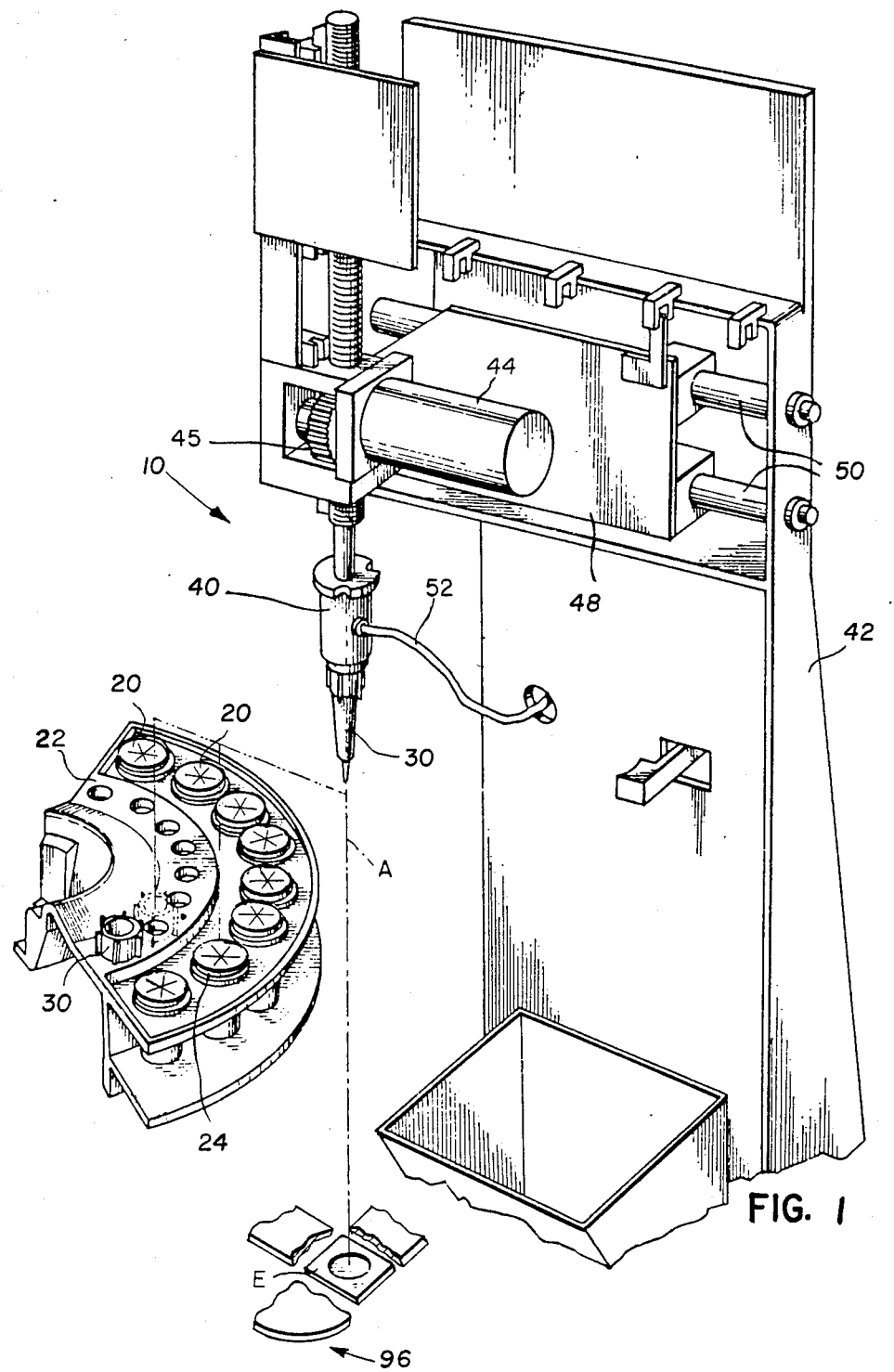
FIG. 1 is a fragmentary perspective view of a dispensing apparatus with which the method of the invention can be practiced.
Figure 2:
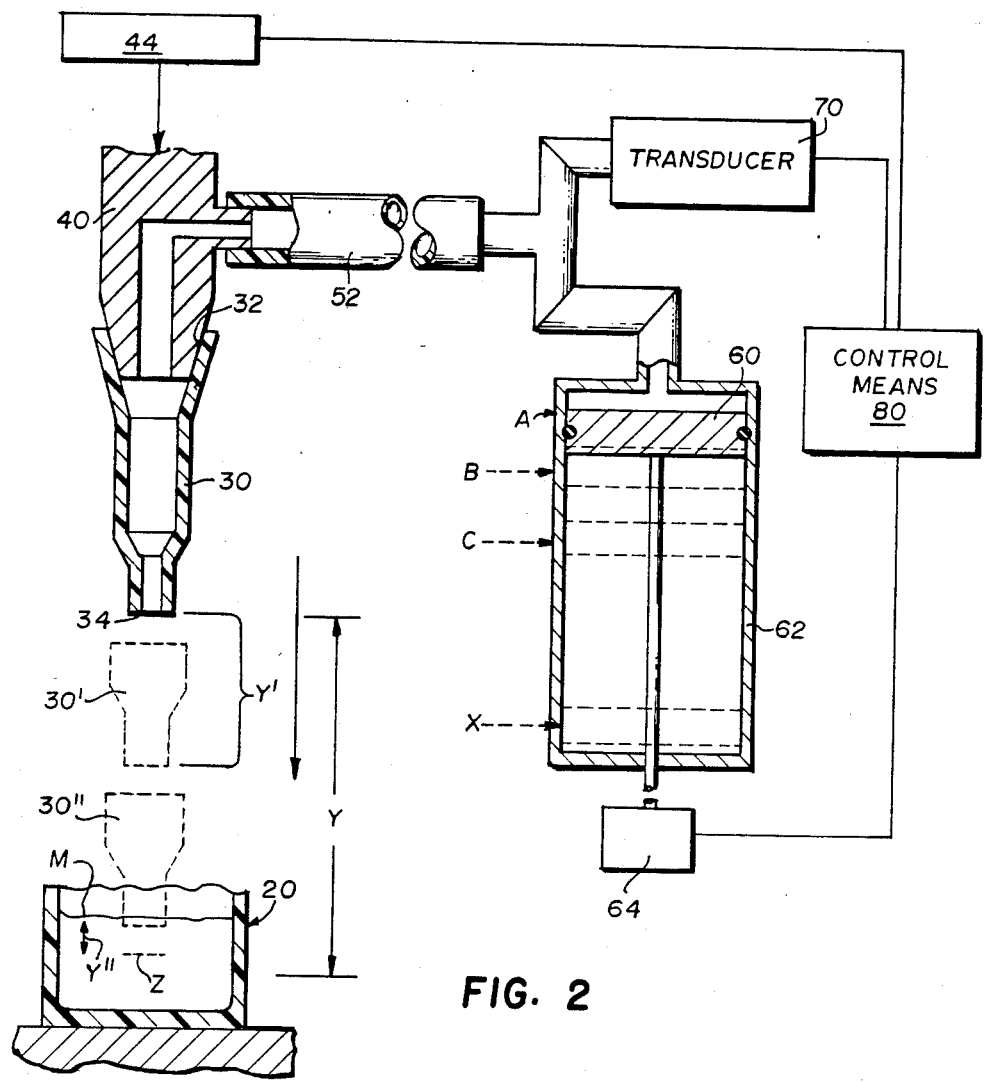
FIG. 2 is a fragmentary, partially schematic view illustrating the steps of the method, wherein parts and positions are not shown to scale.

A portion of a preferred dispensing apparatus 10 is illustrated in FIGS. 1 and 2. A plurality of relatively large sample containers 20 is provided in a tray 22, which also supports removable, disposable dispensing containers 30. The containers 30 have, FIG. 2, a larger aperture 32 at one end to mate with the probe, and a smaller aperture 34 at the opposite end for aspirating and dispensing. Each of containers 20 is preferably provided with a pierceable closure or cap 24, FIG. 1. A probe 40 is mounted for vertical and horizontal movement on a frame 42, such movement being provided respectively by a motor 44 and gear 45, and by a car 48 carrying the probe 40 horizontally on rails 50. Motor 44 can be a stepper motor or a D.C. motor with feedback control. The combined movement of the car and probe is effective to carry the probe within the plane noted as "A", FIG. 1.

A pressure line 52 provides a partial vacuum or a partial pressure, relative to atmospheric, to a dispensing container 30 picked up by the probe. The pressure or vacuum is provided by means such as a piston 60 and piston chamber 62, FIG. 2, driven by appropriate motor means 64. For example, movement of piston 60 from position "A" down to position "X" creates the operative partial vacuum that aspirates the liquid from container 20 into container 30 at the appropriate time. A pressure transducer 70 is used to sense the pressure in container 30, for example to determine when proper dispensing of the liquid out of container 30 occurs.

Alternatively, piston chamber 62 and its piston can be part of probe 40 so as to move up and down with the probe.

Figure 3:
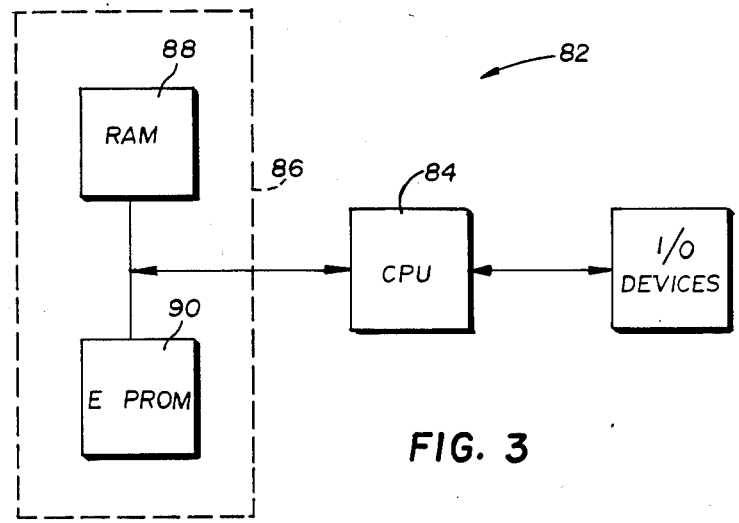
FIG. 3 is a schematic illustration of a microprocessor useful as a control means.

Appropriate control means 80 are provided to coordinate the actuation of motor 44 and motor 64, in response to conditions sensed by e.g., transducer 70. Control means 80 can comprise a microprocessor or hard-wired logic circuits. Most preferably, it includes a microprocessor 82, FIG. 3, particularly in light of the programming discussed hereinafter. As is conventional, such a microprocessor comprises a central processing unit 84, for example, an Intel 8086 chip, and memory unit 86 comprising one or more RAM's 88 and optionally one or more E PROM's 90. The microprocessor preferably is also wired to standard input/output devices, as shown, if the dispensing apparatus is part of a complete analyzer.

In accord with one aspect of the invention, the aforesaid apparatus is used as follows to detect the penetration of the liquid meniscus M, FIG. 2, by the aperture 34 of container 30: Assume the total distance from aperture 34 to a point that will always penetrate the liquid (the minimum fill) is initially dimension Y. (This dimension is obtained with container 30 already penetrated through any cap on container 20, FIG. 1.) While container 30 is still at atmospheric pressure, the reference value needs to be established. This can be done two different ways: the signal generated by the pressure transducer before motor 64 is activated can be taken as the value indicative of atmospheric pressure, since in fact container 30 and tube 52 are in fluid contact both with the atmosphere and transducer 70. Or alternatively, while container 30 is still at atmospheric pressure because the container is still at separation dimension Y, piston 60 is moved from the solid position shown as "A", FIG. 2, to the first dotted position shown as "B" to generate a partial vacuum that is sufficient, if liquid were interfaced with aperture 34 of container 30, to generate a signal indicative of equilibrium pressure of such liquid. (As used herein, "equilibrium" refers to the liquid meniscus formed in the apparatus being stationary.) The partial vacuum so generated is used to generate a reference signal from transducer 70 that is indicative of no liquid having been encountered, since the first test is by definition at atmospheric pressure. Next, motor 44 is activated to advance container 30 a fraction Y' of dimension Y, for example 24% of that dimension. Practically, Y'/Y is between about 1/5 and ⅓. Motor 44 is stopped by control means 80, and motor 64 activated again to move piston 60 from position B to position C. The amount of partial vacuum so generated need not be, but preferably is, the same as in moving from position A to B. A signal is again produced by transducer 70, and that signal is compared to the reference signal previously generated. If there is no difference greater than a predetermined threshhold amount (to accommodate noise), then the liquid meniscus M still has not been penetrated. This is represented by container position 30', FIG. 2.

The aforementioned incremental advance of the probe, followed by a fractional partial vacuum being drawn by the piston, is repeated until either (a) a transducer signal is generated at a new level that exceeds the predetermined threshhold value, thus indicating the penetration of meniscus M (container 30" in FIG. 2), or (b) the increments advanced exceed a safety factor, m. That is, eventually piston 60 will advance to position X in chamber 62, and insufficient withdrawal of the piston will remain to permit aspiration of the liquid once the liquid is encountered. To prevent this from happening, if the liquid is not sensed after a prescribed number of attempts, either piston 60 is reset to its position A or the probe is lowered the remaining portion of dimension Y presumed to be effective to penetrate the liquid at its nominal level. The use of a transducer signal that exceeds the threshhold value to sense the liquid penetration is based upon the known principle that the resistance of a column of liquid to a partial vacuum is significantly different than the resistance provided by air.

By way of further explanation, the partial vacuum needed to sense for liquid penetration, that is, that which is sufficient to generate a signal indicative of the equilibrium pressure of any present liquid, depends upon a number of well-known factors which include: the dimensions of container aperture 34, the surface tension of the liquid, the contact angle at the liquid-container interface, and the corners encountered by the liquid entering the container. The measurement of the pressure is also affected by the presence of a transient and a steady state component. The transient component has a decreasing pressure profile with a time constant that is a function of the liquid viscosity and of the resistance to flow of the liquid within aperture 34. The amplitude of the transient will be a function of the ratio of the change in volume to the total internal air volume. The maximum value of the steady state component will be a function of the contact angle at the liquid-container interface and the internal radius of the container opening at such interface. The contact angle is a characteristic of the liquid/container material combination. The more hydrophobic the material of the container, the greater the contact angle and the greater the equilibrium pressure generated by the presence of liquid in aperture 34. Preferably, the pressure measurement is made at a time, after the volume change, which is selected to give the most consistent readings for the variety of liquids to be encountered by the dispensing apparatus. With hydrophobic container materials, most liquids will produce a large, stable equilibrium pressure reading. Liquids with low contact angles may be read shortly after the volume change at a time much longer than the settling time of the air component of the transient but well before the end of the liquid component of the transient.

It will be readily evident that more than the vacuum needed to produce an "indicative" signal can be used, but that such excessive vacuums are less desirable because, (a), they use up more of the pump volume, and (b) they tend to produce a longer transient signal. For most biological liquids of interest, the partial vacuum sufficient to produce the indicative signal is a fraction only of the operative partial vacuum used to initiate aspiration. For a particular set of container and liquid parameters, it has been found, for example, that the partial vacuum to produce the "indicative" signal occurs at about 1/5 the level of vacuum used to initiate aspiration of the liquid into that container. As used herein, "indicative" means, capable of being detected as an unambiguous event.

When the transducer signal indicates liquid penetration, motor 44 is activated one more time, to prepare container 30 for aspiration. Specifically, the motor advances aperture 34 of container 30 further (distance Y") into the liquid to position Z. The amount of advance is the amount needed to be certain that, during aspiration, aperture 34 still remains below meniscus M. Otherwise, there could be insufficient liquid above aperture 34 to be certain the liquid is aspirated without any air bubbles.

Thereafter, piston 60 is withdrawn to position X, FIG. 2, causing aspiration of the liquid into the container.

Probe 40 is then vertically withdrawn from container 20 and car 48 pulled back so that container 30 is vertically aligned with, e.g., a test element E held by suitable holding means 96, FIG. 1. Container 30 is then lowered until the liquid can be dispensed onto the test element. Dispensing occurs from the operative partial pressure generated by moving piston 60 from position X toward position A, preferably in 10 $\mu$l steps, each step for a separate test element.

The procedure of activating the piston to sense for liquid only when container 30 is not advancing, is preferred because the sensing of the liquid penetration is more complex if done while container 30 is advancing towards the liquid.

Figure 4:
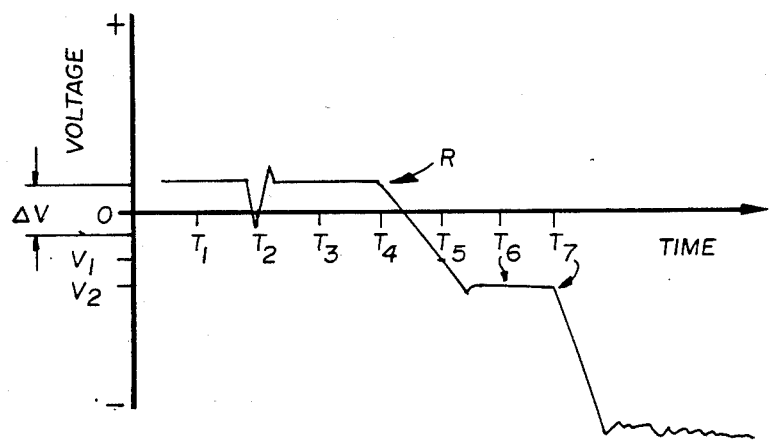
FIG. 4 is an example of a signal trace generated by the transducer when carrying out the steps of the invention.

FIG. 4 is a representative signal produced by a transducer 70 when practicing the invention. In this case, only fractional partial vacuums were used to sense for the penetration event, that is, piston 60 was moved stepwise away from position A towards position X. Container 30 was constructed in accordance with U.S. Pat. No. 4,347,875, issued Sept. 7, 1982, with an inside diameter of aperture 34 that was about 500 $\mu$m. In the trace, time $t_1$ represents the time at which the voltage signal was read while the container was at atmospheric pressure, to establish a reference value R. Or alternatively, that value can be read at time $t_3$, the steady state condition after the first partial vacuum is taken by moving at time $t_2$ piston 60 from position A to position B. The trace indicates a slight transient change in pressure when piston 60 moves at time $t_2$. The microprocessor 82 subtracted from voltage R a predetermined threshhold value $\Delta V$, here about 100 mv. The threshhold value $\Delta V$ was set to exceed the transient portions of the signal noted above. Additionally, it also was set to exceed the noise created by pressure changes arising from extraneous events. For a test signal to be representative of the condition of air-liquid interface penetration, this $\Delta V$ had to be exceeded. At time $t_3$, motor 44 was activated to move container 30 an incremental distance Y' towards the liquid. At time $t_4$, piston 60 was moved to position C, and in fact the signal dropped well beyond the threshhold value $\Delta V$, indicating penetration had occurred. Preferably, the steady state value $V_2$ is read at time $t_6$, as in FIG. 4, but with the proper selection of $\Delta V$, the increasing signal producing at time $t_5$ a transient value $V_1$ is also useful. That is, any value $V_1$ that negatively exceeds $\Delta V$ can be used to trigger the event of liquid penetration. After time $t_6$, probe 40 advanced the preset distance Y" described above, and at time $t_7$, aspiration commenced.

The rate at which the condition of aperture 34 is sensed, and the rate of advance of probe 40 towards the liquid, are not critical, and are a function of the length of time available for a given sample test. By way of example, the total time for the iterative sensing of penetration and of moving the probe, up to the point where piston 60 is activated to aspirate the liquid, can be 800 millisec. Conventional stepper motors are available to cause the probe to advance in steps of $\frac{1}{8}''$ toward the liquid with each step taking only 100 millisec. The time needed to form a fractional partial vacuum or fractional partial pressure and to allow the transducer to generate a pressure signal is about 50 millisec. Thus, 5 such iterations can be done within the allotted 800 millisec. Alternatively, a longer time can be set aside with more or fewer iterations.

Figure 5:
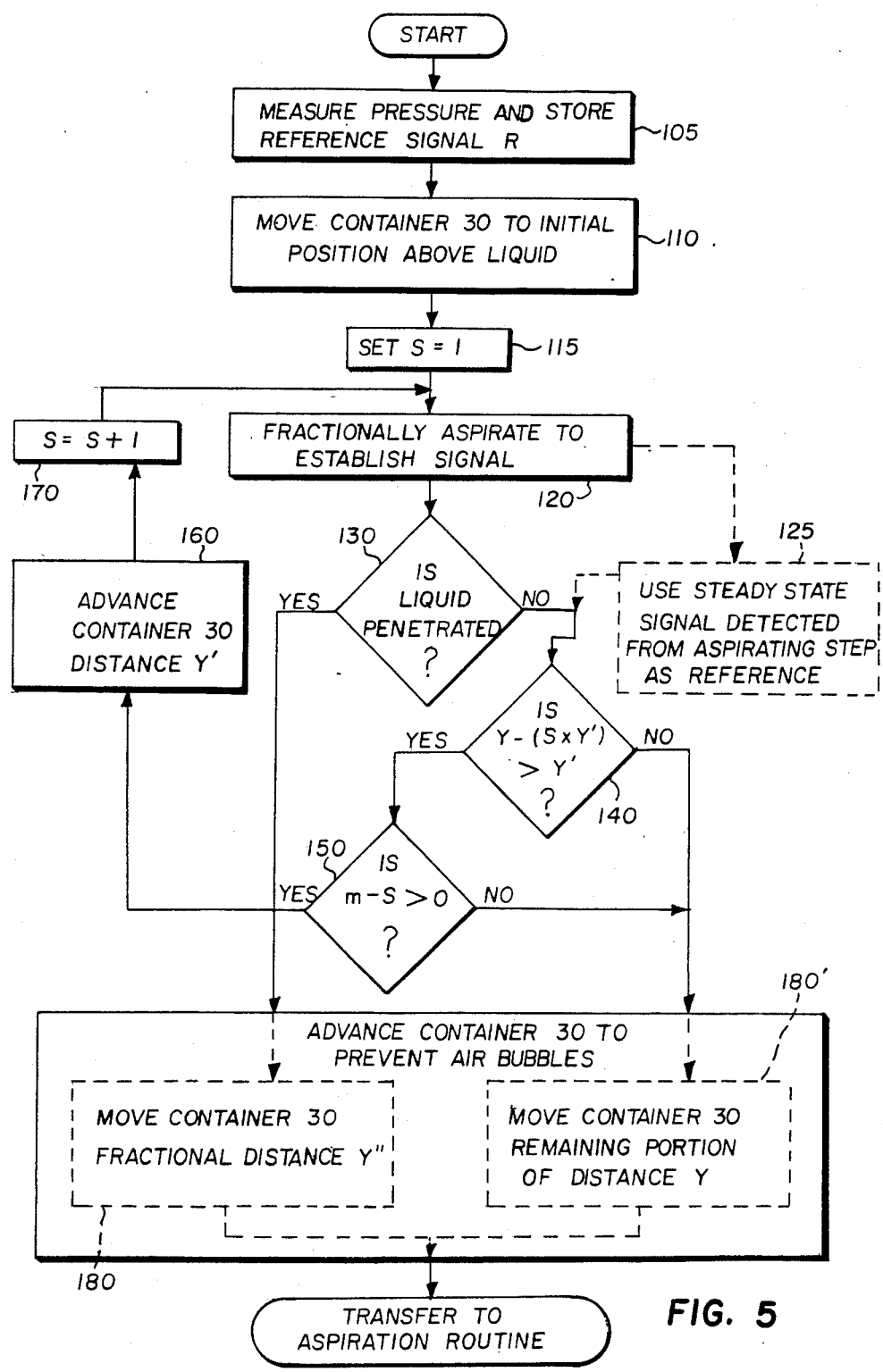
FIG. 5 is a flow chart for programming the control means of the described apparatus to carry out the invention.

It will be appreciated that control means 80 is programmed or hard-wired to provide the timing described above. FIG. 5 is a flow chart that is useful in programming microprocessor 82, using conventional programming techniques. Specifically, the first step 105 is preferably to read the transducer signal while the container 30 is at atmospheric pressure, and storing the read value as reference R. The next step 110 is to move container 30 to an initial position at distance Y above the minimum level of liquid, FIG. 2, by activating motor 44. (Distance Y is subject to variations based upon the dimensions of container 20.) Such initial position is usually a location wherein container 30 has pierced the cap 24, FIG. 1, of the container. Next, step 115, S is set equal to 1. In step 120, motor 64 is activated (e.g., 12 half steps) to fractionally aspirate to generate a signal through the pressure sensing by the pressure transducer. If the reference R has not been read as step 105, then alternative step 125 is followed to obtain R. That is, the signal so generated by step 120 is selected, step 125, to be the reference signal ("R", FIG. 4) because it has been generated while the container is known to be at atmospheric pressure. If alternative step 125 is followed, then the program stores the reference value "R" and goes directly to step 140. Otherwise, step 130, the program tests to see if the liquid has been penetrated. If the answer is negative, then container 30 is ready to advance a distance Y', FIG. 2, if there remains a multiple greater than 1 of Y' left in the distance container 30 has to travel to completely traverse dimension Y. To test this, the microprocessor queries in step 140 the relationship $Y-(S\times Y')>Y'$. If the answer is yes, the microprocessor further queries, step 150, whether $m-S>0$, where m is the maximum number of fractional aspirations, discussed above, that has been predetermined to be safe and still have sufficient volume left in chamber 62, FIG. 2, to do the operative aspiration of the liquid. For example, m can=4. If step 150 is answered yes, then motor 44 is activated, step 160, to advance container 30 a distance Y' (for example by advancing 66 half-steps). The loop then returns to step 120 via step 170 for the next iteration of the process.

Returning to step 130, if that query is answered in the positive, then the program exits from the aforedescribed loop. Preferably, an additional step 180 is included to advance container 30 a distance Y" to position Z, FIG. 2, prior to aspiration, as described above, to prevent air bubbles from being drawn in during aspiration.

The other route out of the loop occurs if the query of either step 140 or 150 is answered in the negative. The loop is exited and a preferred additional step 180' is to advance or move container 30 the remaining portion of distance Y to position it at a location presumed to penetrate the liquid at a depth that insures aspiration will occur without drawing in air bubbles.

Alternatively, step 180 can be modified to occur in stages as part of the aspiration routine which follows. That is, the aspiration step can proceed fractionally with further fractional advances of the container into the liquid. Thus, the aspiration can proceed by motor 64 and piston 60 withdrawing a portion only of the desired liquid, e.g., for 10 half-steps, followed by motor 44 advancing container 30 by a small amount, e.g., 1 half-step. Then, motor 64 withdraws piston 60 another 10 half-steps, and motor 44 advances 1 half-step etc., until all of the required liquid has been aspirated. As will be readily apparent, the amount of advance of container 30 is adjusted per amount of aspiration, based upon the diameter of container 20, to be sure aperture 34 of container 30, FIG. 2, is kept below meniscus M.

Alternatively, step 180' can be modified, when exiting from step 150 only, so that, instead of moving container 30 the remaining distance, piston 60 is reset to its initial position, e.g., position A, and sensing continues as described above. (S is reset to 1.)

Other than as noted above, the aspiration routine following liquid sensing is conventional.

As noted above, sensing for liquid penetration while container 30 continues to advance introduces additional complexities. However, although not preferred, the invention can still be practiced by repeated sensing for liquid at spaced intervals, while still moving container 30 toward the liquid. In that case, it is possible the liquid will be penetrated after a portion of the partial vacuum has already been dissipated while still in air, producing therefore a smaller negative steady-state signal response $V_2$, FIG. 4. Such value $V_2$ might be less negative than $(R-\Delta V)$. In that case, the sensing protocol should be modified to either (a) use the transient value $V_1$ that exceeds the threshhold $\Delta V$, or (b) reduce the threshhold value $\Delta V$.

In yet another alternative, the pressurizing means can be operated so as to alternate between pressurizing and aspirating, to sense whether the liquid meniscus M has been penetrated. In such an embodiment, after the reference signal is generated by piston 60 moving to position B from position A, and probe 40 has been lowered one increment of distance Y, piston 60 is returned to position A rather than being moved to position C, FIG. 2. This acts to generate a fractional partial pressure in container 30 which forces air out of aperture 34. The signal generated by transducer 70 in the case where no liquid is encountered by the expelled air is different (at a lower voltage level) than the signal that occurs when the air has to be forced out into liquid. This alternative has the advantage that piston 60 automatically resets back to position A after every other incremental advance of the probe, so that no special resetting is necessary after a large number (m) of failures to detect the interface. It has the disadvantage, however, of potentially bubbling air into the sample liquid, if the penetration occurs before the half cycle when a partial pressure, rather than a partial vacuum, is used to generate the test signal. It has been found that even a slight bubbling of air into the test liquid is unsatisfactory in certain analyses as it can alter the level of an analyte of interest.

In still another alternative embodiment, piston 60 is operated to generate only fractional partial pressures to sense for the presence of the liquid. In such an embodiment, piston 60 preferably starts at an intermediate position such as position C, and incrementally advances to position A. If the liquid is still not sensed, piston 60 is reset to the first position, say position C, or the probe is moved the remaining portion of dimension Y where it will have penetrated the liquid.

In still another alternative embodiment, the reference signal produced for comparison with the signal sensing whether penetration has occurred or not, is produced while the dispensing container has its dispensing aperture immersed in a reference liquid. The signal so produced is stored in the microprocessor and a $\Delta V$ threshhold is added thereto, to represent the signal that is indicative of the dispensing container at atmospheric pressure. That is, any signal produced that is more positive than the value produced by adding $\Delta V$, is indicative that the air-liquid interface has not yet been penetrated by the dispensing container.

It will be appreciated that the aforedescribed methods allow the detection of the penetration of the liquid by container 30, so that subsequent aspiration occurs with a minimum of exterior wetting of the container. This in turn minimizes the possibility of perfusion.

The invention has been described in detail with particular reference to preferred embodiments thereof, but it will be understood that variations and modifications can be effected within the spirit and scope of the invention.

What is claimed is:

1. In apparatus for aspirating and dispensing liquid and including a probe for removably mounting a container having an aspirating and dispensing aperture; pressurizing means fluidly connected to said probe for generating an operative pressure differential relative to atmospheric pressure, effective to aspirate or dispense liquid into or from a mounted container; and moving means for advancing said probe and such mounted container toward, and away from a nominal level location;
   an improved aspiration control system comprising
   (a) means for controlling the advance of said probe in increments,
   (b) means for actuating said pressurizing means only when said probe is not advancing, to generate a pressure differential in such container, relative to atmospheric pressure, that is sufficient to indicate whether such container aperture is closed by the liquid,
   (c) means for detecting and signalling the pressure produced within such container by said pressure differential; and
   (d) means for comparing the signalled pressure against a reference value determinative of the presence of liquid in such container aperture, said control system further being free of any valve means interposed between said pressurizing means and said detecting means.

2. In apparatus for aspirating and dispensing liquid and including a probe for removably mounting a container having an aspirating and dispensing aperture; pressurizing means fluidly connected to said probe for generating an operative pressure differential relative to atmospheric pressure, effective to aspirate or dispense liquid into or from a mounted container; and moving means for advancing said probe and such mounted container toward, and away from, a nominal liquid level location;
   an improved aspiration control system comprising
   (a) means for controlling the advance of said probe in increments;
   (b) means for actuating said pressurizing means only when said probe is not advancing, to produce a partial vacuum or a partial pressure within such dispensing container that is sufficient to generate a signal indicative of equilibrium pressure of liquid at a liquid-container interface, if liquid is present,
   (c) means for forming said signal characteristic of said partial vacuum or partial pressure produced in step (b), and
   (d) means for comparing said signal of step (c) against a reference signal characteristic of said partial vacuum or said partial pressure when generated with such dispensing container either at atmospheric pressure or penetrated into the liquid, to determine whether said signal of step (c) is indicatve of such dispensing container being at atmospheric pressure or is indicative of such dispensing container having penetrated the liquid, and for repeating the functions provided by said means (a) through (c) up to a predetermined limit, or until said signal produced by means (c) is indicative of such dispensing container having penetrated the liquid, said control system further being free of any valve means interposed between said pressurizing means and said detecting means.

3. A method for detecting that a dispensing container of an aspirating and dispensing apparatus has penetrated into a liquid through an air-liquid interface, said apparatus including a probe for removably mounting a container having an aspirating and dispensing aperture; pressurizing means fluidly connected to said probe for generating an operative pressure differential relative to atmospheric pressure, effective to aspirate or dispense liquid into or from a mounted container; and moving means for advancing said probe and such mounted container toward, and away from, a nominal liquid level location;
   the method comprising the steps of
   (a) controlling the advance of said probe in increments,
   (b) actuating said pressurizing means only when said probe is not advancing, to generate a pressure differential in such container, relative to atmospheric pressure, sufficient to indicate whether such container aperture is closed by the liquid,
   (c) detecting and signalling the pressure produced within such container by said pressure differential;
   (d) comparing the signalled pressure against a reference value determinative of the presence of liquid in such container aperture, and
   (e) after detecting the presence of liquid in said container, aspirating liquid into the container by actuating said pressurizing means, whereby asid method avoids the necessity of switching from one pressurizing means for step (c) to another pressurizing means for step (e).

4. A method for detecting that a dispensing container of an aspirating and dispensing apparatus has penetrated into a liquid through an air-liquid interface,
   said apparatus including a probe for removably mounting a container having an aspirating and dispensing aperture; pressurizing means fluidly connected to said probe for generating an operative pressure differential relative to atmospheric pressure, effective to aspirate or dispense liquid into or from a mounted container; and moving means for advancing said probe and such mounted container toward, and away from, a nominal liquid level location;

the method comprising the steps of (a) controlling the advance of said probe in increments, (b) actuating said pressurizing means only when said probe is not advancing to produce a partial vacuum or a partial pressure within such dispensing container that is sufficient to generate a signal indicative of equilibrium pressure of liquid at a liquid-container interface, if liquid is present, (c) forming said signal characteristic of said partial vacuum or partial pressure produced in step (b), (d) comparing said signal of step (c) against a reference signal characteristic of the pressure in such dispensing container when said container is either at atmospheric pressure or penetrated into the liquid, to determine whether said signal of step (c) is indicative of such dispensing container being at atmposheric pressure or is indicative of such dispensing container having penetrated the liquid, (e) if said signal formed in step (c) is within a threshold value of being indicative of such dispensing container being at atmospheric pressure, then repeating said steps (a) through (d) up to a predetermined limit, or until said signal of step (c) is indicative of such dispensing container being penetrated the liquid, and (f) after detecting the presence of liquid in said container, asperating liquid into the container by actuating said pressurizing means, whereby said method avoids the necessity of switching from one pressurizing means for step (c) to another pressurizing means for step (e).

5. A method as defined in claim 4, wherein said comparing step (d) comprises the step of comparing the signal formed in step (c) with said reference signal generated in such container while at atmospheric pressure, and wherein said signal of step (c) is indicative of such dispensing container having penetrated the liquid when such signal of step (c) differs from said reference signal by a threshhold amount.

6. A method as defined in claim 4, wherein said partial vacuum or pressure used in step (b) is a fraction of said operative vacuum or pressure.

7. A method as defined in claim 4, wherein said step (b) comprises the step of aspirating only to generate a partial vacuum, whereby the liquid to be aspirated is not subject to bubbling as would be the case if a partial pressure were generated to detect said interface.

8. A method as defined in claim 4, and after step (e), the additional step of:

(f) advancing such dispensing container an amount that will insure aspiration of the liquid without air bubbles.

9. A method as defined in claim 8, wherein said advancing step comprises the step of moving such container an additional distance into said liquid that corresponds at least to said desired amount to be aspirated, whereby when the liquid is aspirated, it is not lowered below the liquid entry point of such dispensing container.

10. A method as defined in claim 8, wherein said advancing step (f) comprises the step of moving such container the remaining portion of said maximum possible distance.

11. A method as defined in claim 8, wherein said step (f) comprises the steps of repeatedly advancing such dispensing container further into the liquid after a portion of the liquid is aspirated and before the next portion is aspirated, until all the desired liquid has been aspirated.

12. In apparatus for aspirating and dispensing liquid and including a probe for removably mounting a container having an aspirating and dispensing aperture; pressurizing means fluidly connected to said probe for generating an operative pressure differential relative to atmospheric pressure, effective to aspirate or dispense liquid into or from a mounted container; and moving means for advancing said probe and such mounted container toward, and away from, a nominal liquid level location;

an improved aspiration control system comprising (a) means for controlling the advance of said probe in increments, (b) means for actuating said pressurizing means only when said probe is not advancing, to produce a partial vacuum or a partial pressure within such dispensing container that is sufficient to generate a signal indicative of equilibrium pressure of liquid at a liquid-container interface, if liquid is present, (c) means for forming said signal characteristic of said partial vacuum or partial pressure produced in step (b), and (d) means for comparing said signal of step (c) against a reference signal characteristic of said partial vacuum or said partial pressure when generated with such dispensing container either at atmospheric pressure or penetrated into the liquid, to determine whether said signal of step (c) is indicative of such dispensing container being at atmospheric pressure or is indicative of such dispensing container having penetrated the liquid, and for repeating the functions provided by said means (a) through (c) up to a predetermined limit, or until said signal produced by means (c) is indicative of such dispensing container having penetrated the liquid, said control system further being free of any valve means interposed between said pressurizing means and said detecting means, and means for alternating said actuating means (b), during each repetition of step (a) through (c), so that for one repetition a partial vacuum is formed, the next repetition a partial pressure is formed, the next repetition a partial vacuum is formed, repeatedly through the repetitions, so that said actuating means need not be specially reset at a starting point after a large number of failures to detect the container having penetrated the liquid.

13. A method for detecting that a dispensing container of an aspirating and dispensing apparatus has penetrated into a liquid through an air-liquid interface, said apparatus including a probe for removably mounting a container having an aspirating and dispensing aperture; pressurizing means fluidly connected to said probe for generating an operative pressure differential relative to atmospheric pressure, effective to aspirate or dispense liquid into or from a mounted container; and moving means for advancing said probe and such mounted container toward, and away from, a nominal liquid level location;

the method comprising the steps of (a) controlling the advance of said probe in increments,
(b) actuating said pressurizing means only when said probe is not advancing to produce a partial vacuum or a partial pressure within such dispensing container that is sufficient to generate a signal indicative of equilibrium pressure of liquid at a liquid-container interface, if liquid is present,
(c) forming said signal characteristic of said partial vacuum or partial pressure produced in step (b),
(d) comparing said signal of step (c) against a reference signal characteristic of the pressure in such dispensing container when said container is either at atmospheric pressure or penetrated into the liquid, to determine whether said signal of step (c) is indicative of such dispensing container being at atmospheric pressure or is indicative of such dispensing container having penetrated the liquid,
(e) if said signal formed in step (c) is within a threshold value of being indicative of such dispensing container being at atmospheric pressure, then repeating said steps (a) through (d) up to a predetermined limit, or until said signal of step (c) is indicative of such dispensing container being penetrated the liquid, said step of repeating steps (a) through (d) including the step of alternating the actuation of said pressurizing means so that, first, a partial vacuum is formed, then, a partial pressure, then, a partial vacuum, each time step (b) is carried out for as many repetitions as are necessary, so that said actuating means need not be specially reset at a starting point after a larger number of failures to detect the container having penetrated the liquid, and
(f) after detecting the presence of liquid in said container, aspirating liquid into the container by actuating said pressurizing means, whereby said method avoids the necessity of switching from one pressurizing means for step (c) to another pressurizing means for step (e).

14. A method as defined in claim 13, wherein said partial vacuum or pressured used in step (b) is a fraction of said operative vacuum or pressure.

15. A method as defined in claim 13, and further including, after detecting the presence of liquid in said container, the step of:
(g) advancing such dispensing container an amount that will insure aspiration of the liquid without air bubbles.

16. A method as defined in claim 15, wherein said advancing step comprises the step of moving such container an additional distance into said liquid that corresponds at least to said desired amount to be aspirated,
whereby when the liquid is aspirated, it is not lowered below the liquid entry point of such dispensing container.

17. A method as defined in claim 15, wherein said advancing step comprises the step of moving such container the remaining portion of said maximum possible distance.

18. A method as defined in claim 15, wherein said step (g) comprises the steps of repeatedly advancing such dispensing container further into the liquid after a portion of the liquid is aspirated and before the next portion is aspirated, until all the desired liquid has been aspirated.

* * * * *